United States Patent [19]
Rauch

[11] Patent Number: 5,265,165
[45] Date of Patent: Nov. 23, 1993

[54] MULTIPURPOSE HEADWEAR

[76] Inventor: Robert A. Rauch, 21621 Fernleaf, El Toro, Calif. 92630

[21] Appl. No.: 879,159

[22] Filed: Apr. 30, 1992

Related U.S. Application Data

[63] Continuation of Ser. No. 495,690, Mar. 16, 1990, abandoned.

[51] Int. Cl.⁵ .............................................. H04R 5/02
[52] U.S. Cl. ..................................... 381/25; 381/183; 381/187; 381/190; 2/10; 2/12; 2/209.13; 2/906; 2/918
[58] Field of Search ................. 2/10, 12, 175, 177, 2/199; 381/183, 187, 190

[56] References Cited

U.S. PATENT DOCUMENTS

| | | | |
|---|---|---|---|
| 1,543,094 | 6/1925 | Blecker et al. | 2/199 |
| 1,673,859 | 6/1928 | Wittcoff | 2/175 |
| 1,735,705 | 11/1929 | Wittcoff | 2/10 |
| 2,474,386 | 6/1949 | Volkmann | 381/187 |
| 2,810,022 | 10/1957 | Finken et al. | 381/187 |
| 3,346,876 | 10/1967 | Hutton | 2/177 |
| 3,696,357 | 10/1972 | Kilgore | 381/187 |
| 3,786,519 | 1/1974 | Aileo | 381/187 |
| 4,259,747 | 4/1981 | Taesler et al. | 381/187 |
| 4,403,120 | 9/1983 | Yoshimi | 381/183 |
| 4,456,797 | 6/1984 | Olsen | 381/25 |
| 4,551,584 | 11/1985 | Mathiasen | 381/183 |
| 4,565,258 | 1/1986 | Butler et al. | 381/25 |
| 4,638,207 | 1/1987 | Radice | 310/328 |
| 4,682,363 | 7/1987 | Goldfarb et al. | 381/187 |
| 4,727,599 | 2/1988 | Rappaport et al. | 381/187 |
| 4,776,044 | 10/1988 | Makins | 381/187 |
| 4,821,323 | 4/1989 | Papiernik | 381/25 |
| 4,856,689 | 8/1989 | Horton | 381/187 |
| 4,864,619 | 9/1989 | Spates | 381/183 |
| 4,961,227 | 10/1990 | Le Donne | 381/25 |
| 5,046,192 | 9/1991 | Ryder | 2/12 |

FOREIGN PATENT DOCUMENTS

| | | | |
|---|---|---|---|
| 0284199 | 12/1986 | Japan | 381/190 |
| 0109881 | 5/1925 | Switzerland | 2/10 |

Primary Examiner—Forester W. Isen
Attorney, Agent, or Firm—Michael Sand Co.

[57] ABSTRACT

Headwear that produces sound from a signal is provided by an audio device in addition to the normal features of the headwear. The audio headwear of the present invention may be configured as a visor, goggles or a headband. In a preferred embodiment, the present invention is an audio visor comprising a flexible body, a protective layer and two speaker elements. The speaker elements are attached between the flexible body and the protective layer attached to cover the bottom side of the flexible body. Thus, the speaker elements do not interfere with the operation of flexible body as a visor. The preferred embodiment also comprises conductor leads and an amplifier to adapt the output of the audio device for the speaker elements. In the second embodiment, the audio headwear further comprises a lens attached to the flexible body to form goggles or sunglasses.

40 Claims, 9 Drawing Sheets

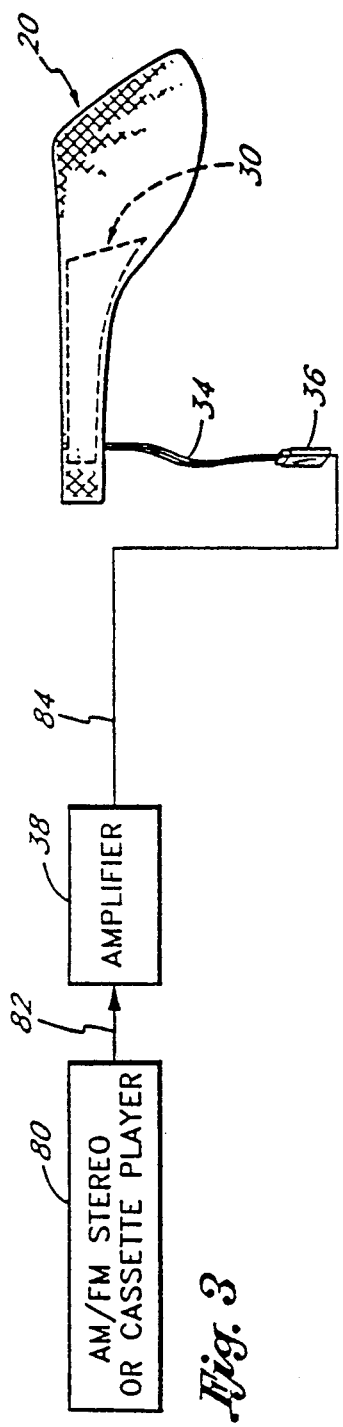
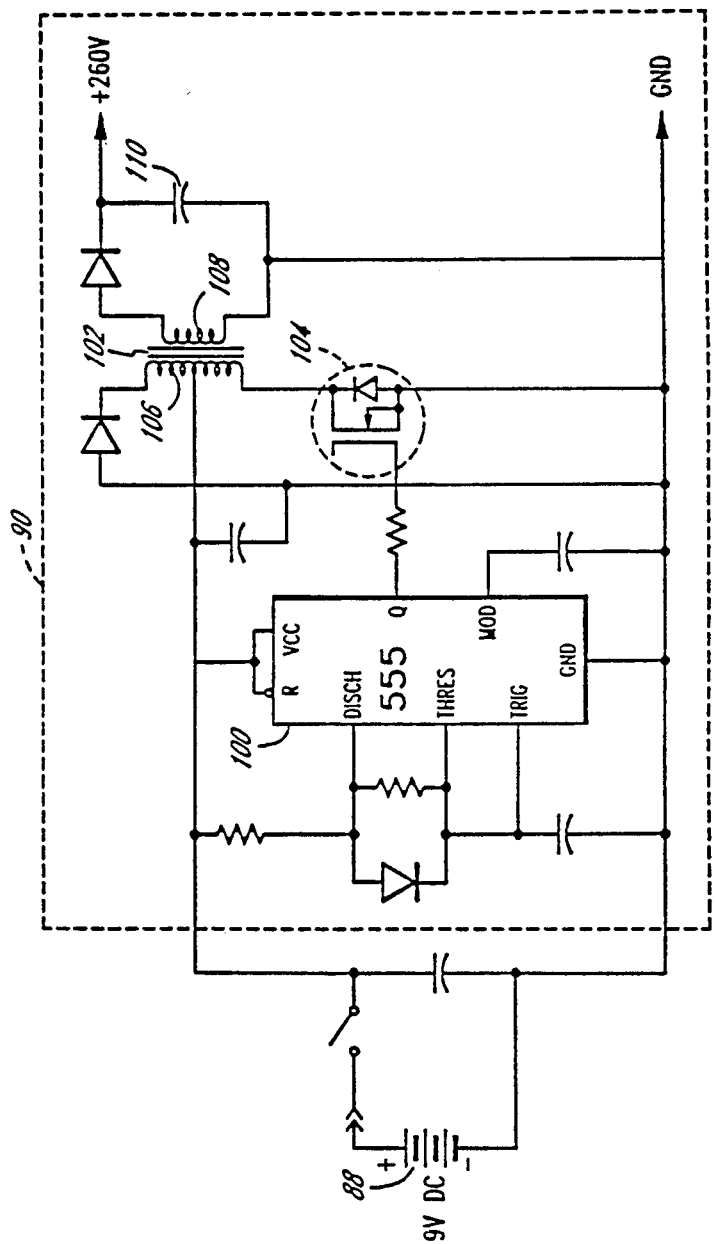

MULTIPURPOSE HEADWEAR

This application is a continuation of application Ser. No. 07/495,690, filed Mar. 16, 1990, now abandoned.

BACKGROUND OF THE INVENTION

The present invention relates generally to wearing apparel and particularly to headwear, such as visors, headbands or glasses that perform several functions. Still more particularly, the present invention relates to headwear that contains earphones or headphones.

Headphones are known for converting electrical signals produced by an AM/FM radio or cassette tape player into sound waves. Their use has dramatically increased with the advent of portable AM/FM radios and cassette tape players of reduced size. Typically, headphones include a pair of earphones or speaker elements. The earphones are placed directly over the opening of the ear or inserted into the ear canal of the user. Such placement of the earphones tends to block other background or warning sounds, such that they are difficult to hear over the sound produced by the earphones. This is particularly undesirable for persons engaged in sports activities like skiing, biking or jogging where conversation or other background sounds can provide warning of potentially hazardous situations.

The headphones known in the art are also uncomfortable for many users to wear because of the positioning of the earphones. The earphones can become particularly uncomfortable when wedged inside the user's ear as required for proper operation of some earphones. The pressure on the ears from headphones that cover the ear opening can also cause discomfort for the user, particularly when used for extended periods of time. If used during sports activities, the headphones can also be easily dislodged from the ears, causing the user's attention to be directed from the sports activity and creating a potentially hazardous situation.

Using headphones while wearing other headwear such as a hat, visor, headband or glasses can also create other problems. For example, headphones can be awkward and unmanageable when used simultaneously with headwear. Removing and putting on headphones and headwear are hampered when the two are used together. Moreover, headwear can interfere with the proper operation of the headphones and vice versa. For example, headwear often fits improperly when used with headphones.

As a result there is a need for headphones that comfortably fit the user and operate properly without interfering with the useful features of headwear.

Similarly, even sunglasses can interfere with the proper operation of other headwear such as a hat, visor or headband. The application and removal is especially a problem when sunglasses and other headwear are used together. Thus, a need exists for a device that has both the features of sunglasses and a visor.

SUMMARY OF THE INVENTION

The present invention comprises an item of wearing apparel capable of performing several functions. In the preferred embodiments the wearing apparel is capable of producing sound from an electrical signal, and includes a sheet of a first material, a sheet of a second electrically responsive material and a pair of electrical leads. The first material forms wearing apparel and has a surface in proximity to an ear of a user. The second material is mounted in juxtaposition to the first material with at least a portion of the second material free to acoustically vibrate. The leads are connected to the second material and conduct a signal which drives the second material to vibrate so as to produce sound.

Preferred embodiments of the present invention are in the form of audio headwear. In the first embodiment, an audio visor comprises a flexible body, a protective layer and two speaker elements that use piezoelectric film. A brim and a pair of straps are integrally formed from the flexible body. The speaker elements are attached on a bottom side of the flexible body. The speaker elements and the bottom side of the flexible body are then covered with the protective layer for a comfortable fit on the user's head. The speaker elements advantageously utilize piezoelectric film for producing sound because of its light weight, durability and high quality sound reproduction.

In a second embodiment, the audio visor includes a lens and a nosepiece to form goggles. The lens is preferably tinted and functions as sunglasses to provide protection from the sun. The second embodiment may also be formed without speaker elements and still operate as a visor and sunglasses.

In the third embodiment, a pair of ear pods are attached to the audio visor. Each ear pod includes an acoustic reflection member and a comfort strip. The ear pods are attached on opposite sides of the visor below the speaker elements to enhance the quality of the sound produced.

In the fourth embodiment, the present invention is configured as a head band. The head band includes a flexible body in the shape of a strip with two enlarged portions to cover the ears of the user and to place the speaker elements near the ears. A protective layer of the same shape is attached on the bottom side of the flexible body to give the head band a comfortable fit.

BRIEF, DESCRIPTION OF THE DRAWINGS

FIG. 3 is a block diagram of the coupling of the audio visor of FIG. 1 to a prior art audio device;

FIG. 4A is a schematic diagram of the forward converter portion of the amplifier of the present invention;

DESCRIPTION OF THE PREFERRED EMBODIMENTS

The present invention comprises wearing apparel that includes earphones for producing sound from an audio device. The earphones are preferably positioned within the wearing apparel and do not interfere with normal use and operation of the wearing apparel. Several preferred embodiments of the wearing apparel illustrating different types of headwear such as a visor, goggles or a headband are described below.

Figure 1:
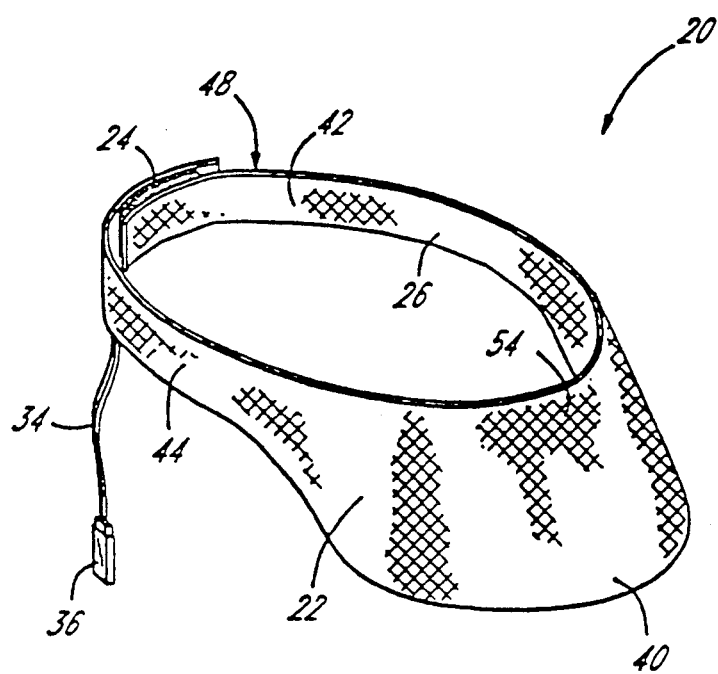
FIG. 1 is a perspective view of a first embodiment of the present invention as an audio visor.
Figure 2:
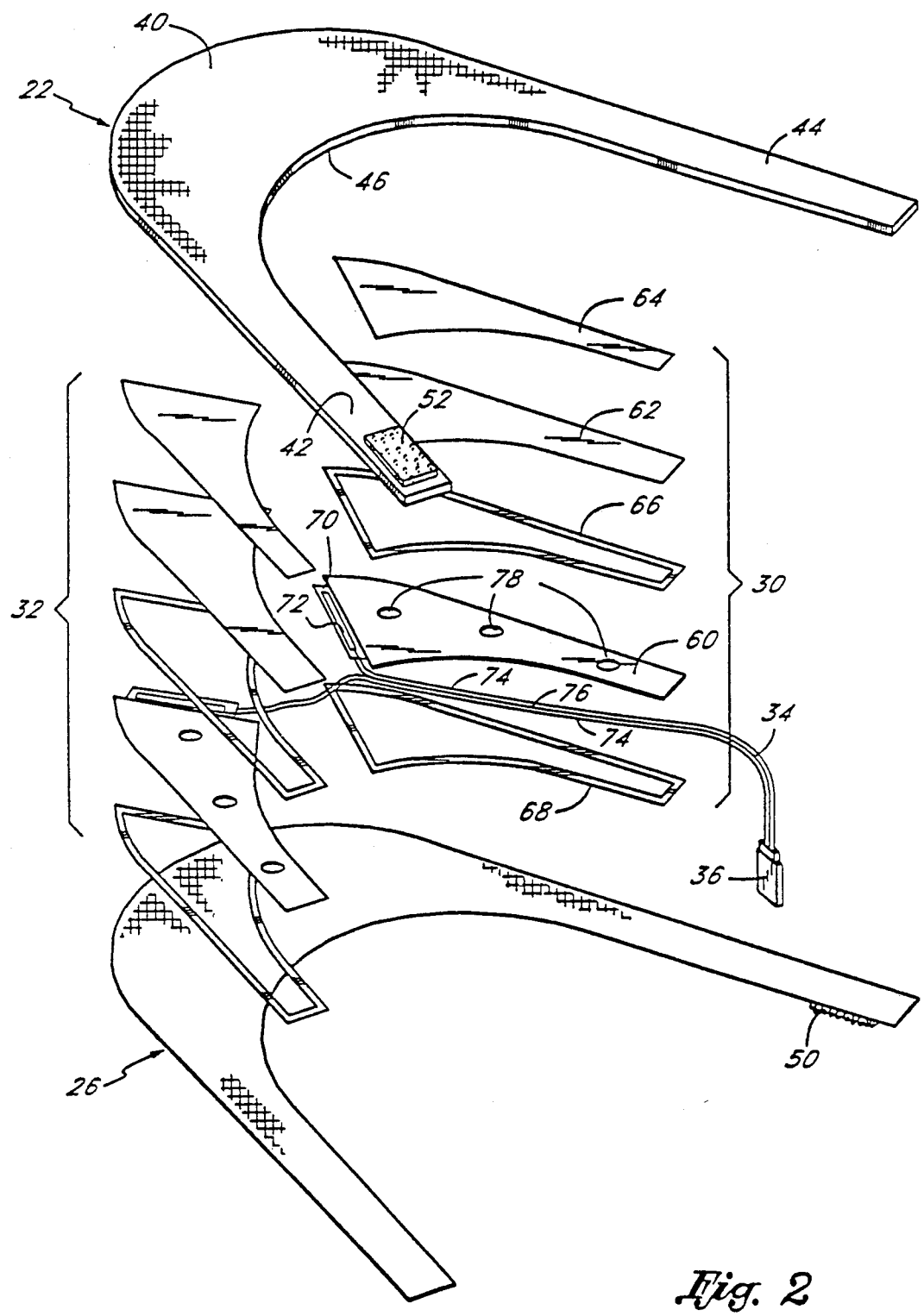
FIG. 2 is an exploded perspective view of audio visor of FIG. 1.

Referring to FIG. 1, a first embodiment of the present invention as an audio visor 20 is illustrated. The visor 20 is adapted for attachment to the human head and provides shade from the sun. The audio visor 20 comprises a flexible body 22, a fastener 24 and a protective layer 26. The outer surface of the visor 20 is formed by the flexible body 22 on the top and the protective layer 26 on the bottom. As shown in FIG. 2, the audio visor 20 further includes two speaker elements 30, 32. Conductor leads 34 are connected to the speaker elements 30, 32, and a connector 36 is connected to the conductor leads 34. The speaker elements 30, 32 and a portion of the leads 34 are mounted between the protective layer 26 and the flexible body 22, to hide them from view and prevent them from interfering with the wearing of the visor 20.

In the first embodiment, the flexible body 22 is comprised of a flat sheet with a generally parabolic shape, and includes a brim portion 40, as illustrated in FIG. 2. A pair of straps or side portions 42, 44 extend from opposite sides of the brim portion 40 to permit mounting of the visor 20 on the user's head. The brim 40 has a generally crescent shape so as to provide a shield to protect the user's face from the sun. The straps 42, 44 are generally rectangular strips and comprise the legs of the parabola formed by the flexible body 22.

As shown in FIG. 1, when the visor 20 is in use, the straps 42, 44 and an upper portion 54 of the brim 40 form a generally circular periphery 48 which corresponds to the periphery of the user's head. The straps 42, 44 and the upper portion 54 of the brim 40 are in contact with the user's head, while the remaining portion of the brim 40 extends in a generally horizontal direction which is substantially radially outward from the circular periphery 48.

The flexible body 22 is made of a material sufficiently flexible to allow the straps 42, 44 to be twisted and the brim 40 to be curved for a comfortable fit on the human head. However, the flexible body 22 also has sufficient rigidity for the brim 40 to project in a generally horizontal direction to provide shade from the sun. Preferably, the flexible body 22 is made of wetsuit material approximately 3.0 mm thick. Wetsuit material is advantageous because of its light weight and comfortable fit. In an exemplary embodiment, the flexible body 22 is constructed of neoprene with lycra fabric on the top side. While wetsuit material is preferred, it should be understood that the present invention may be made using other materials.

As mentioned above, the visor 20 includes two speaker elements 30, 32. The speaker elements 30, 32 function as earphones to convert electrical signals into sound waves. As best illustrated in FIG. 2, the speaker elements 30, 32 are made up of layers and have a shape that generally corresponds to the shape of the flexible body 22 in the mounting areas where the brim 40 meets the straps 42, 44. The speaker elements 30, 32 are positioned on the bottom side 46 of the flexible body 22. One speaker element 30, 32 is positioned in each of the two mounting areas so that there is a speaker on each side of the visor 20. The positioning of the speaker elements 30, 32 advantageously provides high quality sound when the visor 20 is worn by the user.

As best illustrated in FIG. 2, the protective layer 26 has parabolic shape corresponding to that of the flexible body 22. The protective layer 26 is mounted on a bottom side 46 of the flexible body 22, so that the speaker elements 30, 32 are between the protective layer 26 and body 22. In the first embodiment, the protective layer 26 is mounted to the bottom side 46 of the flexible body 22 using an adhesive, however, other comparable fastening methods such as sewing or bonding may be used. The protective layer 26 is advantageously sized to cover the entire bottom side 46 of the flexible body 22. The layer 26 protects the speaker elements 30, 32 and also hides them from view. The protective layer 26 is preferably made from a comfortable fabric since it is in direct contact with the user's head when visor 20 is worn. The fabric also allows the sound produced by the speaker elements 30, 32 to pass therethrough relatively unchanged to the user's ears.

A fastener 24 is attached on the flexible body 22 and the protective layer 26 to connect the straps 42, 44 and mount the visor 20 on the user's head. The fastener 24 connects the straps 42, 44 together to form the generally circular periphery 48 that fits against the user's head. In the first embodiment, the fastener 24 is preferably a hook and loop fastener. The hook portion 50 of the fastener 24 is attached on the distal end of the protective layer 26 below the strap 44. The loop portion 52 of the fastener 24 is attached to the top side of the flexible body 22 at the distal end of the other strap 42. The hook portion 50 couples with the loop portion 52 to connect the bottom side of the distal end of the protective layer 26 to the top side of the distal end of the strap 44. Since the distal end of the protective layer 26 is attached on the bottom of the distal end of the strap 42, the fastener 24 effectively connects the bottom side of the strap 42 to the top side of the other strap 44.

The hook 50 and loop 52 portions are advantageously sized to securely fasten the two straps 42, 44 together. The portions 50, 52 have the same size with a width slightly less than that of the straps 42, 44. Preferably, the length of the portions 50, 52 is several inches which advantageously allows for adjustment in the circumference of the circular periphery 48 created when the straps 42, 44 are attached together. Since both portions 50, 52 are several centimeters in length, the amount which the straps 42, 44 overlap can be varied to fit the visor 20 to the size of the user's head while securely fastening the straps 42, 44 together.

Referring to FIG. 2, the speaker element 30 will be described with particularity. It should be understood that the speaker elements 30, 32 are identical except that the left speaker 32 is the mirror image of the right speaker 30. Accordingly, only one of the speakers 30, 32 will be described in detail.

In the first embodiment, each speaker element 30, 32 comprises a film 60, a backing sheet 62, and layers of transfer tape 64, 66 and 68. The film 60, the backing sheet 62, and the layers of transfer tape 64, 66 and 68 are all configured with the same outer shape and size so that they may be placed in the speaker mounting areas between the flexible body 22 and the protective layer 26. The film 60 acts like a diaphragm to translate electrical signals into sound waves. In response to the electrical signals applied, the film 60 deflects in proportion to the voltage applied to produce sound waves. The film 60 is preferably a piezoelectric film. In an exemplary embodiment, the film 60 is a sheet of aluminized Kynar piezo film or high density vinyl fluoride approximately 28 μM thick that is sized to cover an area of the flexible body 22 approximately 5.0 inches in length where the straps 42, 44 and brim 40 meet. Additionally, it has been discovered that the quality of the sound produced by the film 60 is dramatically improved if a series of holes 78 are made in the film 60. The number of holes 78 and the precise positioning of the holes 78 is not critical, but the film 60 functions optimally when the holes 78 are displaced from the edges of the film 60, such that they are located in an area which acoustically vibrates during operation of the speaker. In an exemplary embodiment, there are three holes 78, approximately 0.125 inches in diameter, spaced along the center of the film 60. The film 60 is attached to the backing sheet 62 and then both are mounted inside the visor 20.

On the forward end of the film 60 proximate the brim 40 of the visor 20, the film 60 forms a tab 70. The tab 70 provides an area for the leads 34 to be attached to apply the signal to the film 60. One lead 74 is attached on the top of the tab 70 and another lead 76 is attached on the bottom of the tab 70. Conductive connector strips 72 are provided to electrically connect each lead 74, 76 to the film 60. Although only one strip 72 is visible in FIG. 2, it will be understood that there is a second strip 72 on the bottom of the tab 70. In the first embodiment, the bottom leads 76 of the left and right speaker elements 30, 32 are preferably coupled together and provide a negative return, while the top leads 74 of the left and right speaker elements 30, 32 provide stereo input channels.

The backing sheet 62 is preferably a layer of stiff plastic that provides rigid support for the film 60. In an exemplary embodiment, the backing sheet 62 is a die cut layer of plastic approximately 0.01 inches thick that is also sized for attachment to the flexible body 22. The backing sheet 62 and the film 60 have an identical area and shape.

The layers of transfer tape 64, 66 and 68 have adhesive on both sides for attaching the film 60 and the backing sheet 62. The top layer of transfer tape 64 attaches the bottom side 46 of the flexible body 22 to the top side of the backing sheet 62. The top layer 64 is preferably a solid sheet of transfer tape with the same area and shape as the backing sheet 62 to securely fasten the backing sheet 62 to the flexible body 22.

The middle layer 66 of transfer tape is used to attach the bottom side of the backing sheet 62 to the top side of the film 60. However, the middle layer 66 is not a solid sheet like the top layer 64. Since the middle layer 66 only extends about the periphery of the backing sheet 62, the film 60 is only attached to the backing sheet 62 near the peripheral edges of the film 60. Thus, the backing sheet 62 and the middle layer 66 effectively act as a frame and rigidly attach the film 60 about its periphery which allows those portions of the film 60 interior to its peripheral edges to vibrate and produce good quality sound.

Finally, the bottom layer 68 of transfer tape, which is identical in shape to the middle layer 66, attaches the bottom side of the film 60 to the top side of the protective layer 26. The film 60 is attached to the protective layer 26 in the same manner as it is attached to the backing sheet 62 to ensure that the interior of the film 60 is able to vibrate in response to audio signals.

The middle and bottom layers 66, 68 are preferably made of electrically conductive transfer tape which conducts the audio signal such that it is applied about the entire periphery of the film 60. Such application of the audio signal improves the audio response of the film 60 and generally enhances the sound quality. In an exemplary embodiment, the middle and bottom layers 66, 68 are die cut layers of conductive 3M ® transfer tape. When the 66, 68 are attached on the film 60, they contact the connector strips 72 attached to the tab 70 of the film 60.

While the speaker elements 30, 32 have been described as being attached together using layers of transfer tape 64, 66 and 68, it should be understood that the speaker elements 30, 32 may be assembled using other types of bonding techniques. Moreover, it should be recognized that the speaker elements 30, 32 may be adapted to any variety of shapes that allow the speaker elements 30, 32 to be positioned in between the flexible body 22 and the protective cover 26.

The audio visor 20 of the present invention also includes an amplifier 38 to produce high quality sound from the signals output by an audio device 80 such as an AM/FM stereo or cassette tape player. As best illustrated by the block diagram in FIG. 3, the output of the audio device 80 is coupled through the amplifier 38 to the speaker elements 30, 32 in the audio visor 20. The audio device 80 outputs signals along lead lines 82 to the amplifier 38. The audio device 80 typically outputs signals to provide stereo sound. A right channel signal is provided to drive the right speaker element 30 and a left channel signal for the left speaker element 32. The amplifier 38 modifies the signals received, and outputs signals adapted to drive the speaker elements 30, 32 on lead lines 84. The lead lines 84 are electrically connected to the appropriate speaker element 30, 32 through the connector 36 and the lead lines 34.

The output signals from the audio device 80 are received by the amplifier 38 and modified to a form that will provide enhanced sound quality when the signal is applied to the speaker elements 30, 32. In particular, the amplifier 38 amplifies the signal and performs an impedance matching function. Unlike speakers known in the art, the speaker elements 30, 32 are not inductive but capacitive because of the electrical characteristics of the film 60. Thus, the signal output by the audio device 80, which is designed for inductive speakers, will not produce high quality sound when coupled directly to the speaker elements 30, 32. The signals output by the audio device 80 must be transformed into a signal that will better deflect the film 60 and produce sound.

Figure 4B:
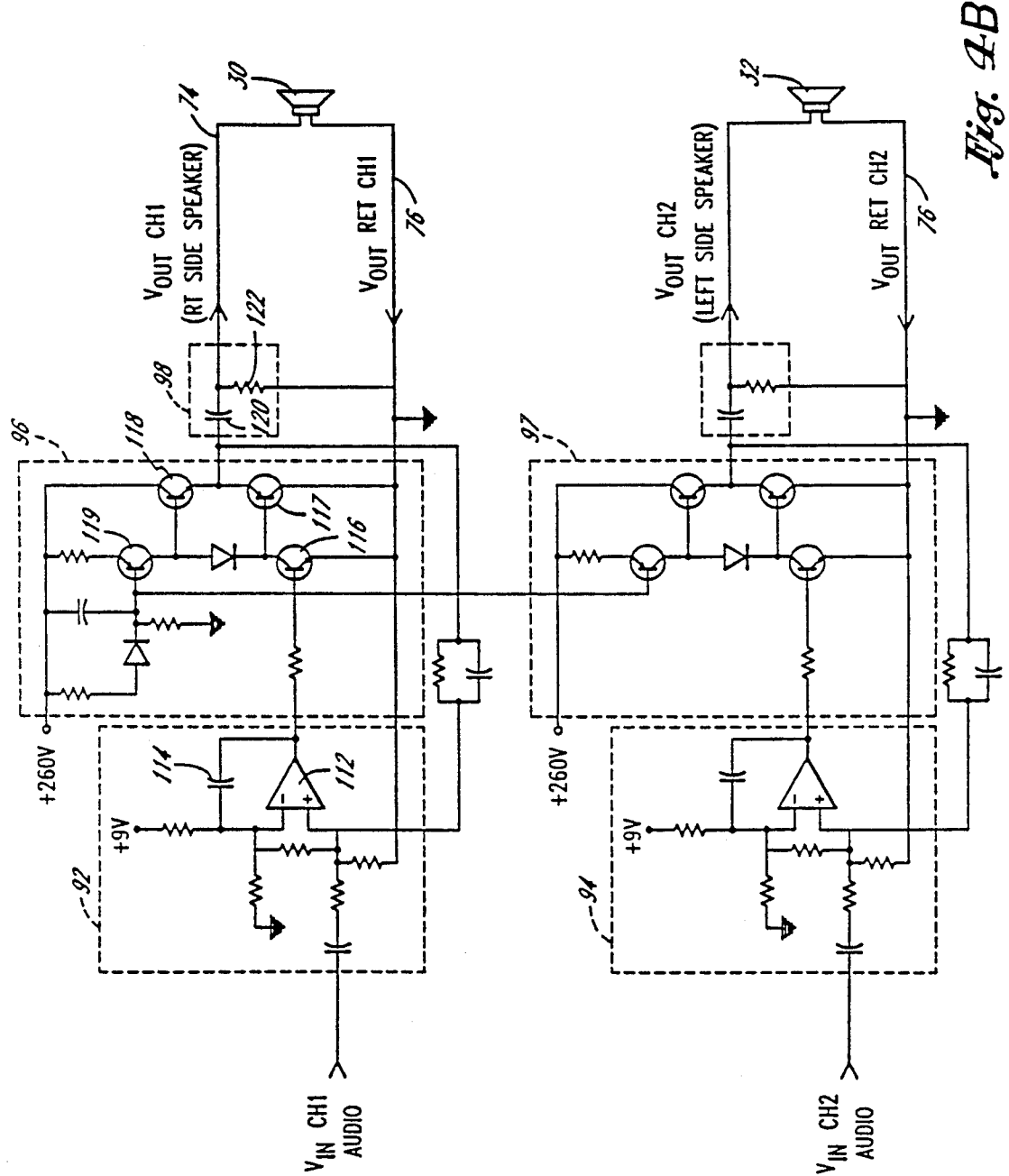
FIG. 4B is a schematic diagram of the amplifier of the present invention.

A circuit diagram for the preferred embodiment of the amplifier 38 is illustrated in FIGS. 4A and 4B. The amplifier 38 comprises a battery 88, a forward converter 90, two integrators 92, 94, two output stages 96, 97 and other passive components. The battery 88 and forward converter 90 provide the voltage required to amplify the signal provided by the audio device 80. The two integrators 92, 94, and two output stages 96, 97 receive and modify the signals output from the audio device 80. With stereo sound, a different signal is provided for each speaker element 30, 32. Thus, the one integrator 92 and the output stage 96 are used to amplify the right channel signal provided to one speaker element 30 and another integrator 94 and output stage 97 are used to amplify the left channel signal provided to the other speaker element 32.

In a preferred embodiment, the forward converter 90 further includes a standard 555 timer 100, a transformer 102 and an electric switch 104. As illustrated in FIG. 4A, the battery 88 supplies a voltage of 9.0 DC volts to the forward converter 90. The forward converter 90 transforms the input voltage into an output voltage of approximately 260 DC volts. The battery 88 is coupled across the series connection of the center tap of a primary winding 106 of the transformer 102 and the electric switch 104. In an exemplary embodiment, the electric switch 104 is a MOSFET. The output of the 555 timer 100 is connected to control the opening and closing of the electric switch 104. The 555 timer 100 is coupled with passive components for a stable operation as an oscillator as well known to one skilled in the art. The electric switch 104 is made to open and close because the output of the timer 100 oscillates between high and low, thus, causing alternating current to pass through the primary of the transformer 102. The transformer 102 is used to step up the 9.0 volts applied to the primary winding to 260 volts output by the secondary winding 108. A capacitor 110 is connected in parallel with the secondary winding 108 to remove any AC components, thus, the forward converter 90 provides a 260 DC volt output.

As shown in FIG. 4B, the 260 volt potential created by the forward converter 90 is used by two output stages 96, 97 and the two integrators 92, 94 to convert the signals from the audio device 80 into a usable form. Preferably, the integrators 92, 94 are identical and output stages 96, 97 are identical. Thus, only the integrator 92 and the output stage 96 for the right channel will be described for simplicity. As illustrated in FIG. 4B, the signal from the audio device 80 is input to the integrator 92. The integrator 92 is formed by an operational amplifier 112, a capacitor 114 and other passive components as known to one skilled in the art. The signal from the audio device 80 is input to through passive components to the positive input of the operational amplifier 112. The output of the integrator 92 is coupled to the input of the output stage 96. The output stage 96 is preferably a Class B output stage formed from four transistors 116–119 as understood by one skilled in the art. In the preferred embodiment, the current source typical in a Class B output stage, is provided by the transistor 119 coupled with other passive components. It should also be noted that the transistors 118, 119 oft he output stage are coupled to the output of the forward converter 90, thereby applying a potential of 260 volts to the output stage 96. The signal output by the output stage 96 is then differentiated by the RC differentiator 98 formed by a capacitor 120 and a resistor 122. The output of the differentiator 98 is then coupled to the speaker element 30.

The integrator 92 receives the signal output by the audio device 80 which has a high voltage output capability for use on inductive speakers. The signal is then integrated by the integrator 92. The output stage 96 then modifies the signal to produce a sizable output current capability or high voltage at low frequency to drive the speaker elements 30, 32. The signal is then differentiated by the RC differentiator 98 to complete the transformation of the signal to one that is equivalent of a current source. Thus, the amplifier 38 basically converts the signal output by the audio device 80 which provides a high voltage output capability for inductive speaker elements to a signal with high current output capability or high voltage at low frequency for capacitive speaker elements.

The present invention will now be discussed with reference to several other embodiments. These other embodiments are often similar to the first embodiment. Thus, where possible, like reference numbers with an "a" suffix have be used to indicate like parts for ease of understanding.

Figure 5:
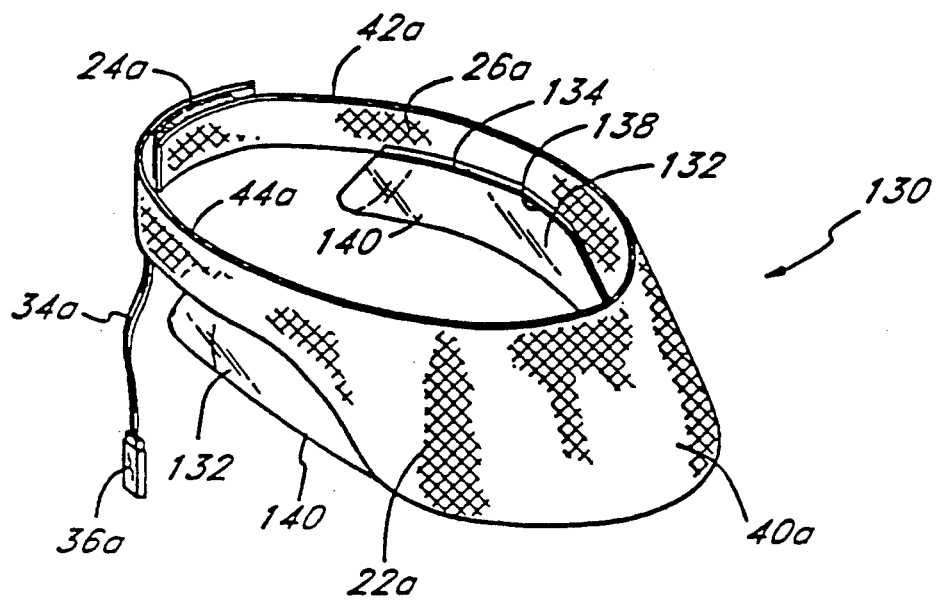
FIG. 5 is a perspective view of a second embodiment of the present invention as goggles.
Figure 6:
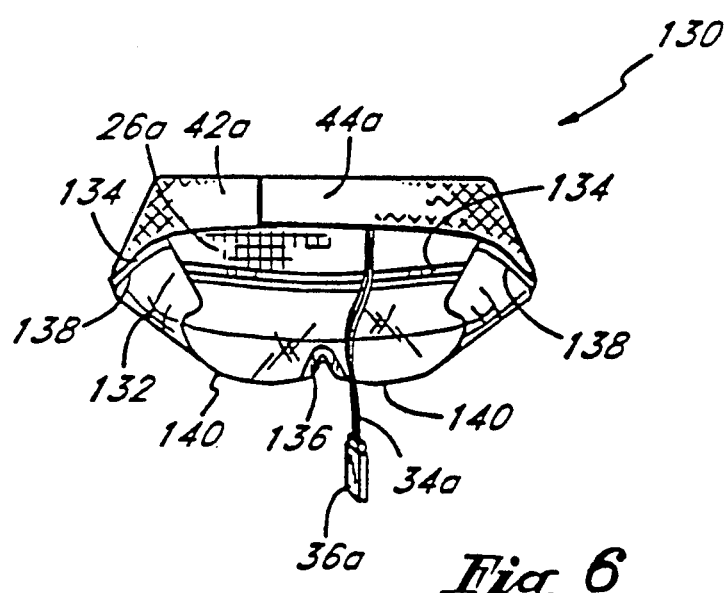
FIG. 6 is a rear elevation view of the goggles of FIG. 5.

Referring now to FIGS. 5 and 6, a second preferred embodiment for the audio headwear 130 is illustrated. The second embodiment 130 is similar to the first embodiment and forms a visor comprising a flexible body 22a, a fastener 24a and a protective layer 26a. The embodiment 130 also includes two speaker elements (not shown), a series of leads 34a and a connector 36a to produce sound from electrical signals. The speaker elements are identical to the speaker elements 30, 32 of the first embodiment described above with reference to FIG. 2. The second embodiment has the same shape as the first embodiment and is formed by attaching the protective layer 26a and the flexible body 22a together, with the speaker elements therebetween.

The visor of second embodiment additionally provides goggles formed by a wrap-around eye shield having a lens 132, a connecting strip 134 and a nosepiece 136. The lens 132 advantageously shades the user's eyes from sunlight. Preferably, the lens 132 is a substantially U-shaped sheet of transparent material which is tinted to reduce the intensity of sunlight, and thereby function as sunglasses. For example, the lens 132 may be cut from a sheet of tinted lexan TM or laminated mylar which advantageously makes the lens 132 flexible, light weight and durable. An upper edge 138 of the U-shaped lens 132 is adapted for attachment to the protective layer 26a. A lower edge 140 of the U-shaped lens 132 parallels the upper edge 138. Near the middle of the lens 132, the lower edge 140 extends in toward the upper edge 138 to provide a triangular notch in the lens 132 for receiving the bridge of the user's nose. The nosepiece 136 is attached along the edge 140 of the triangular area. The nosepiece 136 is preferably made from a piece of wetsuit material sized to cover the edge formed by the triangular area. The lens 132 with the nosepiece 136 attached is adapted to rest upon the bridge of the user's nose for a comfortable fit when the second embodiment 130 is worn.

Figure 7:
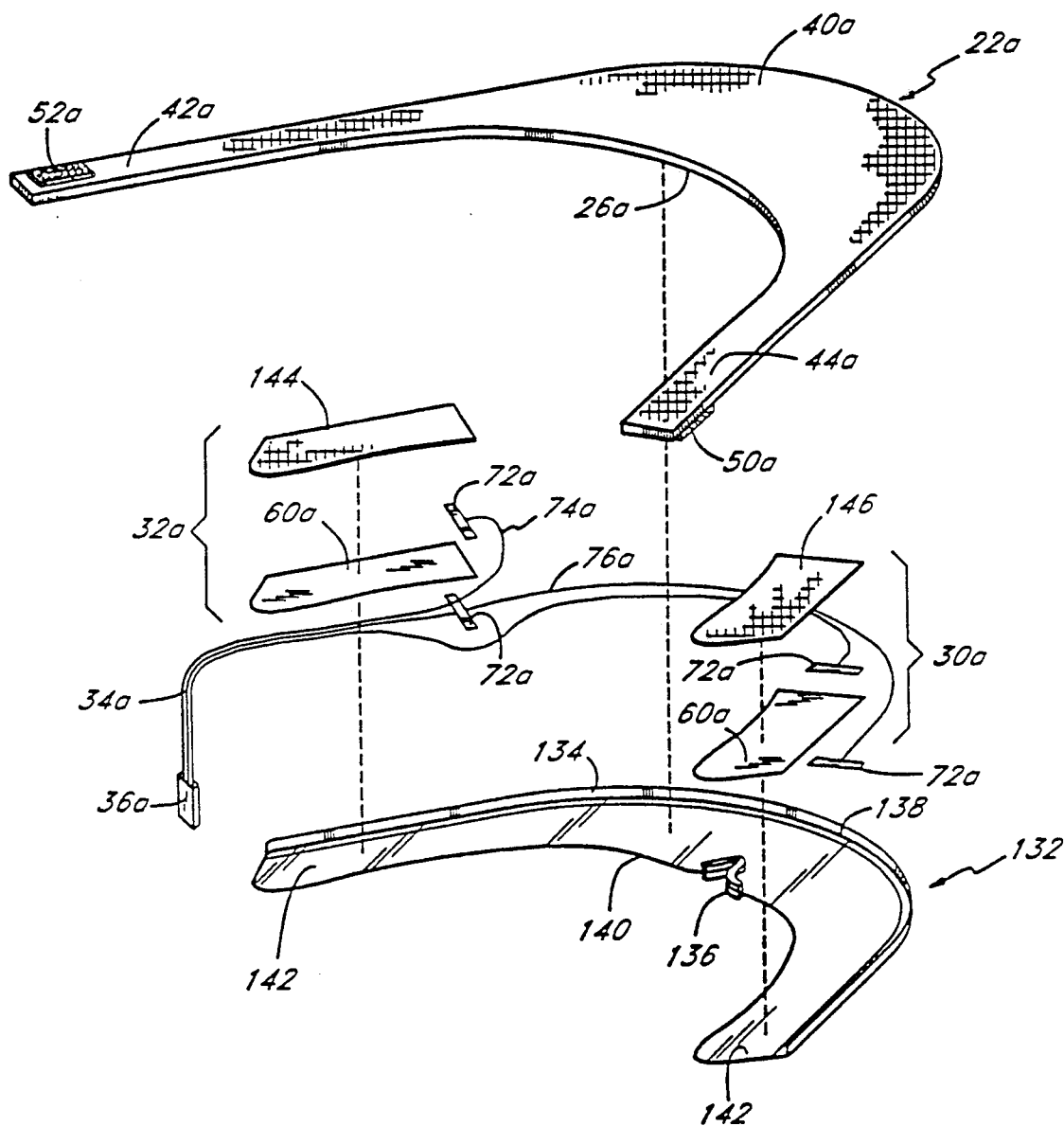
FIG. 7 is an exploded perspective view of the present invention as goggles with an alternate embodiment of the speaker, elements.
Figure 10:
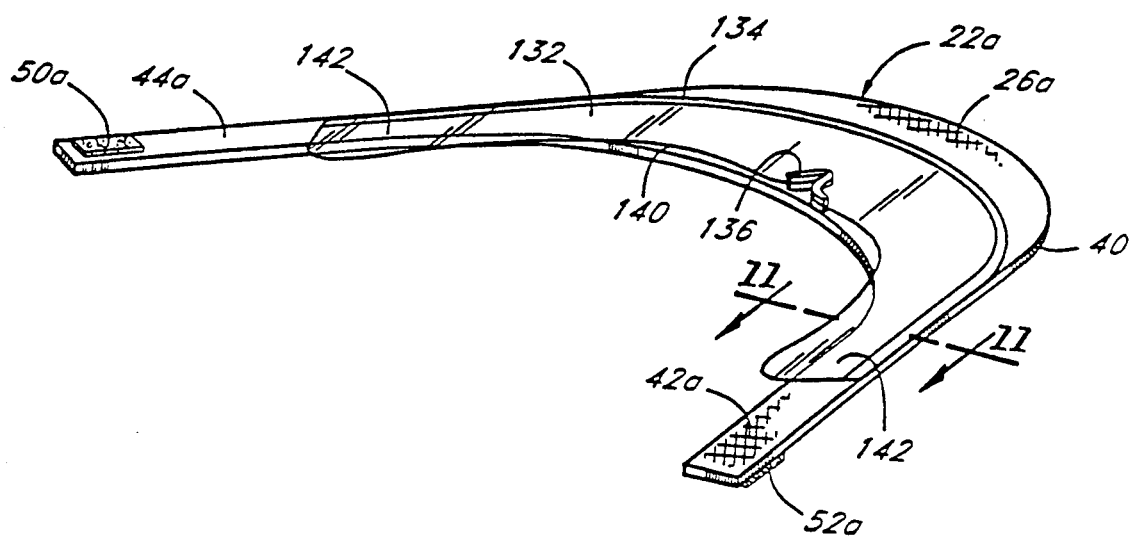
FIG. 10 is a bottom perspective view of the goggles of FIG. 5 in a flat unused position.

As best seen in FIG. 5–7, the lens 132 is attached to the second embodiment 130 using the connecting strip 134. The strip 134 is attached along the upper edge 138 of the lens 132. In a preferred embodiment, the strip 134 extends about 0.25 inches from the upper edge 138 toward the lower edge 140 and covers a small portion of the lens 132. The remaining portion of the strip 134 not attached to the lens 132 is attached on the bottom side of the protective cover 26a as shown in FIG. 6. As best shown in the bottom perspective view of FIG. 10, the strip 134 extends along the entire upper edge 138 of the lens 132 from the strap 42a, across the brim 40a, to the other strap 44a. Thus, the strip 134 has a curved or U-shape similar to the lens 132 and forms an arcuate hinge line.

The connecting strip 134 is preferably made of a fabric material which advantageously creates a flexible hinge. While the connecting strip 134 is described as fabric, it should be understood that the strip 134 may be made of other flexible materials like silicon or polyurethane. As illustrated in the cross sectional view of FIG.

Figure 11:
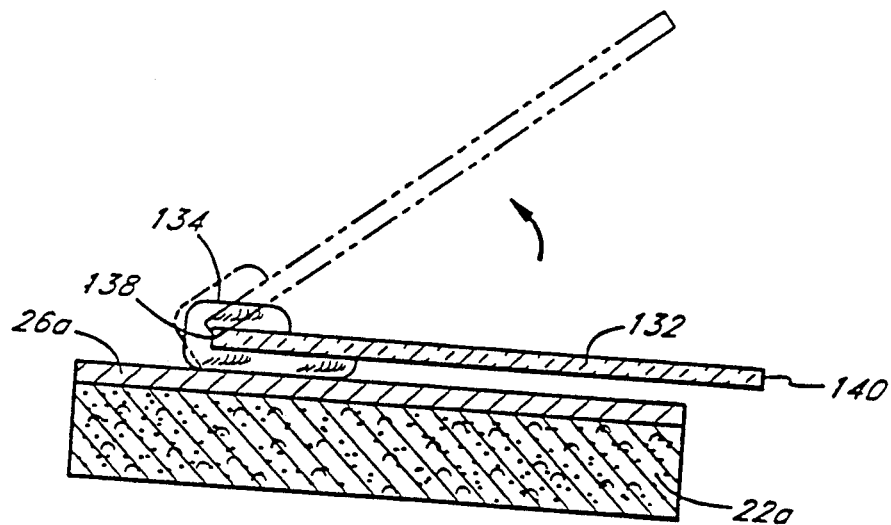
FIG. 11 is a cross-sectional view of the goggles taken along line 11—11 of FIG. 10.

11, the hinge is created by the strip 134 which is folded about the upper edge 138 and attached to the exterior side of the lens 132 and the exterior side of the cover 26a. Since the strip 134 is fabric, it may be attached to the cover 26a and the lens 132 by sewing or adhesive. The hinge allows the lower edge 140 of the lens 132 to swing away from the flexible body 22a and the cover 26a as shown by the phantom lines in FIG. 11.

Figure 12:
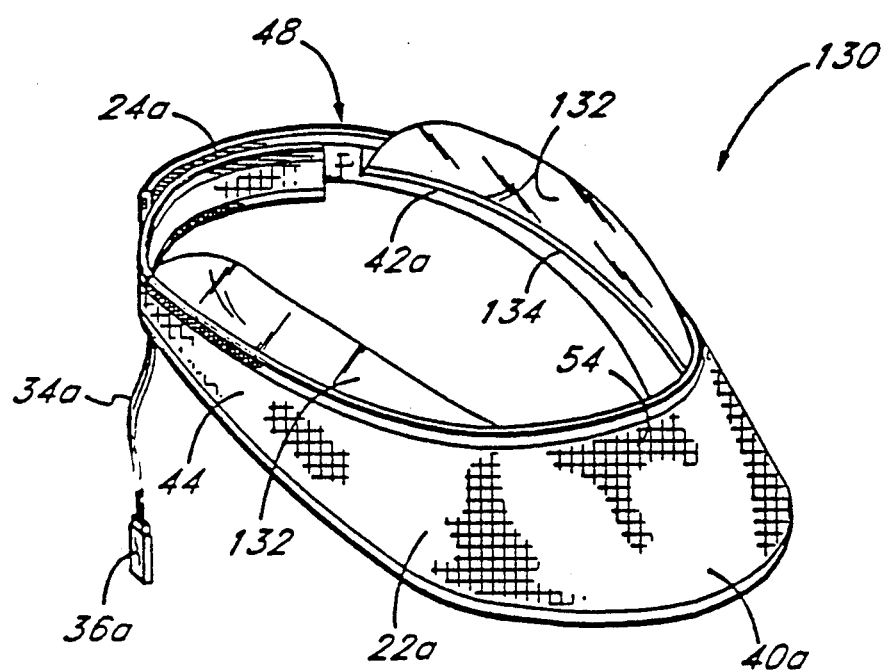
FIG. 12 is a perspective view of the goggles of FIG. 10 with the lens folded up when not in use.

The hinge advantageously allows the lens 132 to be configured in several different positions. For example, if the lens 132 is in use, the hinge permits the lens 132 to project away from the cover 26a and form a wrap around eye shied in an open position as illustrated in FIGS. 5 and 6. The hinge also allows the lens 132 to be contoured to the user's head and lie flat against the cover 26a when the visor is being worn, but the lens 132 is not in use as shown in FIG. 12. When neither the visor nor the lens 132 are used, the visor may be collapsed to lie flat with the lens 132 adjacent to the brim 40a, as in FIG. 10.

The speaker elements are attached in between the protective layer 26a and the flexible body 22a in the same manner as the first embodiment. The lens 132 advantageously improves the sound quality because the lens 132 extends directly beneath the speakers elements. The lens 132 covers and partially encloses the user's ears in an acoustic chamber formed by (i) the flexible body 22a, (ii) the lens 132 and (iii) the user's head when the second embodiment 130 is worn. The sound produced by the speakers is directed down and reflects off the lens 132. Thus, the lens 132 advantageously amplifies and improves sound quality while allowing background noise to enter the acoustic chamber.

In the second embodiment 130, the speakers 30a, 32a may also take an alternate form. The speaker elements 30a, 32a may be mounted directly on the lens 132 as illustrated in FIG. 7. This increases the sound that is provided to the user's ear since the ends 142 of the lens 132 proximate the straps 42a, 44a cover the ears when the second embodiment 130 is worn. The film 60a that forms the speakers 30a, 32a may be placed in very close proximity to the ears by positioning the film 60a directly on the ends 142 of the lens 132. In this alternate form, the film 60a is advantageously shaped to cover an area proximate the ends 142 of the lens 132. This area extends approximately four inches along the upper 138 and lower 140 edges of the lens 132. Placement of the film 60a upon the lens 132 eliminates the need for a backing sheet and the top layer of transfer tape. However, the alternate form of the speakers 30a, 32a utilizes similar assembly techniques as described above with reference to FIG. 2. In particular, a layer of transfer tape (not shown) which forms a strip about the periphery of the film 60a is used to mount the film 60a to the lens 132. The lens 132 and layer of transfer tape cooperate to form a frame for the film 60a in the same manner as the backing sheet 62 and middle layer 66 described above with reference to FIG. 2. The alternate form of the speakers 30a, 32a also retains similar electrical connections, as shown in FIG. 7, to couple the output of the amplifier 38 to the speakers 30a, 32a. This embodiment for the speaker elements 30a, 32a additionally requires a pair of speaker covers 144, 146. As illustrated in FIG. 7, the speaker covers 144, 146 are each place above a respective layer of film 60a. The speaker covers 144, 146 are attached to the film 60a to protect it and the electrical connections as well as provide a comfortable fit.

While the speaker elements for the second embodiment 130 have been described above in great detail, it should be understood that the goggles of the second embodiment may be constructed without the speaker elements and cover 26a and still form multipurpose headwear. The lens 132 would simply be attached directly to the flexible body 22. Without speaker elements, the second embodiment continues to operate as both sunglasses and a visor. It should be noted that the exterior appearance and form of the goggles without speakers elements could be the same as the second embodiment disclosed above.

Figure 8:
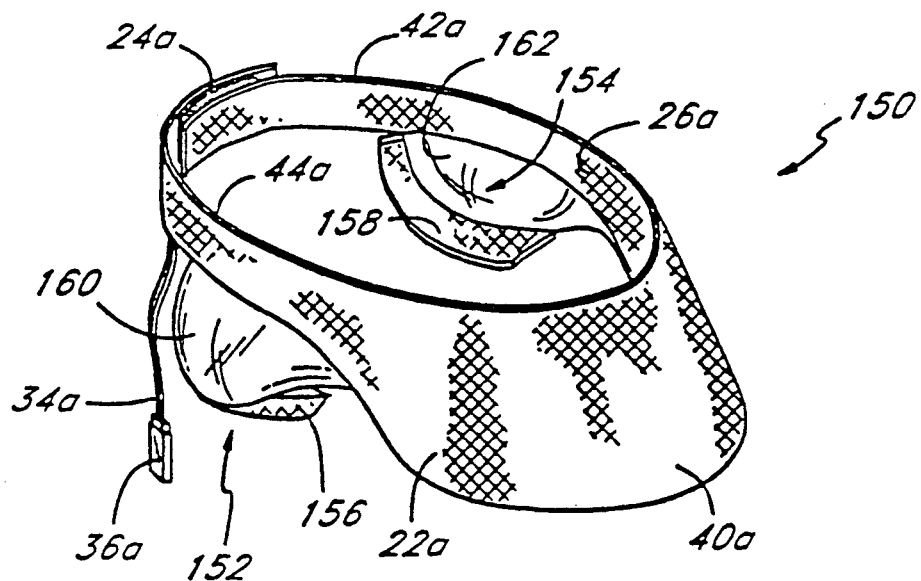
FIG. 8 is a perspective view of a third embodiment of the present invention as an audio visor with ear pods.

Referring now to FIG. 8, a third embodiment 150 of the audio visor is illustrated. The third embodiment 150 of the visor has the same basic structure as the first embodiment with the speaker elements (not shown) attached between the flexible body 22a and the protective layer 26a. However, the third embodiment 150 of the audio visor additionally comprises a pair of ear pods 152, 154 for directing the sound produced by the speakers toward the user's ears when the visor is worn.

Each of the ear pods 152, 154 preferably comprises a comfort strip 156, 158 and a reflecting member 160, 162. One comfort strip 156 and reflecting member 160 are located below the right speaker and the other comfort strip 158 and reflecting member 162 are located below the left speaker. Together each comfort strip 156, 158 and its respective reflecting member 160, 162 form an enclosure or ear pod 152, 154 that enhances sound quality while allowing some background noise to be heard.

The reflecting members 160, 162 are shallow cup structures molded from a sheet of plastic, preferably clear lexan TM. The reflecting members 160, 162 are tear drop shaped to cover the user's ears. Because of the physical properties of the plastic and its cup shape, the reflecting members 160, 162 advantageously absorb little sound and reflect the sound toward the user's ear. Each reflecting member 160, 162 is attached to its respective side of the visor beneath the speaker elements. The reflecting members 160, 162 extend down from the visor and over the user's ears in substantially vertical direction when the visor is worn.

One comfort strip 156, 158 is attached on the bottom edge of each reflecting member 160, 162. The comfort strips 156, 158 are suitable pieces of material adapted for comfort strips 156, 158 are advantageously made of the wetsuit material like the flexible body 22a. Thus, the user is not irritated if the pods 152, 154 contact the area below the ears. The comfort strips 156, 158 have a substantially rectangular shape that is tapered and narrows near one end. A longitudinal edge of the strips 156, 158 is attached to bottom edge of the reflecting members 160, 162 and the reflecting members 110, 112 extend in towards the user's head when the visor is positioned on the head. In this manner, the comfort strips 156, 158 in combination with the reflecting members create a chamber that enhances the sound quality since the sound is directed down from the bottom of the visor toward the ears.

Figure 9:
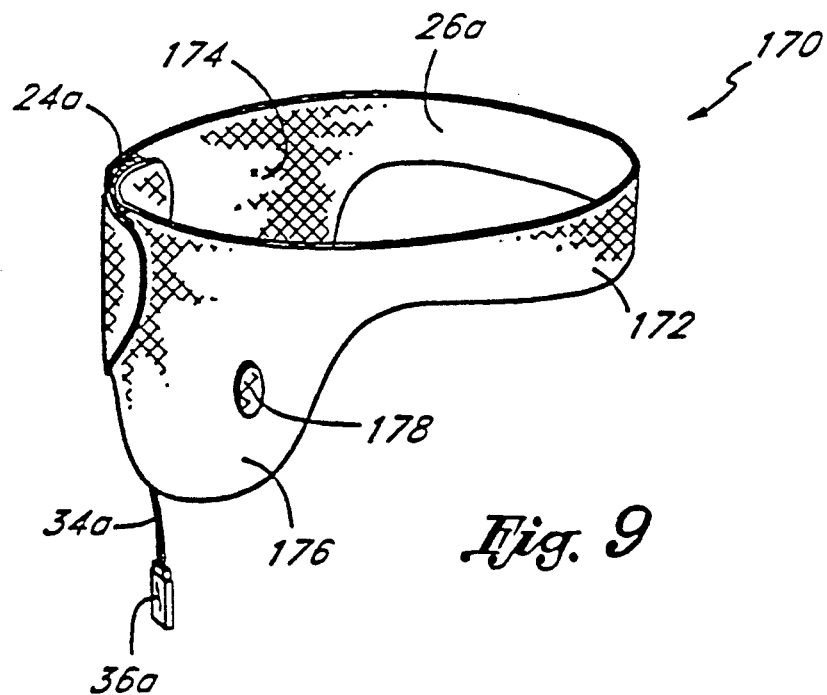
FIG. 9 is a perspective view of a fourth embodiment of the present invention as a head band.

Finally, referring to FIG. 9, a fourth embodiment 170 of the present invention as a headband is illustrated. The headband preferably comprises a flexible body 172, a fastener 24a, a protective layer 26a, and two speaker elements (not shown). A series of leads 34a, and a connector 36a are also included to couple the speaker elements to the audio device 80.

The fourth embodiment 170 is different from previous embodiments primarily because of its shape and function. The flexible body 172, the protective layer 26a and the speaker elements form a strip adapted to be worn about the head and cover the ears. For example, the flexible body 172 is shaped as a slightly curved strip. In an exemplary embodiment, the flexible body 172 is a strip of wetsuit material approximately two inches wide. The flexible body 172 is the same in composition and construction as in other embodiments except that it has a different shape. At two intermediate positions along its length, the flexible body 172 has enlarged portions 174, 176 with a substantially circular shape. The enlarged portions 174, 176 are adapted to cover the ears when the headband 172 is worn. In an exemplary embodiment, the enlarged portions 174, 176 are integrally formed as part of the flexible body 172 and have a diameter of approximately 4.0 inches. Near the center of each enlarged portion 174, 176, an aperture 178 is provided to permit external sounds to enter the ear.

The protective layer 26a is adapted to conform and cover the bottom of the flexible body 172. Thus, the protective layer 26a has the same shape as the flexible body 172 to cover all of bottom side of the flexible body 172. As in previous embodiments, the protective layer 26a is advantageously made of an appropriate fabric for a comfortable fit on the user's head.

The speaker elements of the fourth embodiment 170 have a modified shape. In particular, the speaker elements used in the forth embodiment have a generally circular shape adapted for placement of the speaker elements on the enlarged portions 174, 176 respectively. Additionally, rather than the holes 78 used in the film 60 as described above with reference to FIG. 2, the fourth embodiment 170 has a single hole in the film of the speaker elements corresponding in position to the aperture 178 in the enlarged portions 174, 176 of the flexible body 172. However, the speaker elements have the same layered construction as described with reference to FIG. 2 above with the only distinction being the shape of the elements.

Having described the invention in connection with certain preferred embodiments thereof, it will be understood that many modifications and variations thereto are possible, all of which fall within the true spirit and scope of this invention. In particular, the present invention has been discussed primarily as headwear, but it should be understood that the present invention may be adapted for many different types of wearing apparel. For example, the present invention may be utilized in a jacket with a collar having film and leads attached therein to produce sound.

What is claimed is:

1. An article of headwear, comprising:
   a visor comprising a flexible body, said flexible body being configured to wrap around the head of a user and comprising first and second side portions and a brim portion therebetween, said brim portion having inner and outer edges;
   a bendable eyeshield having an upper edge and a lower edge; and
   a hinge for connecting the upper edge of the eyeshield to the visor along an arcuate hinge line extending along and adjacent to the outer edge of said brim portion, said arcuate hinge line extending from said first side portion along said outer edge of said brim portion to said second side portion, said hinge mounting said eyeshield such that said eyeshield is movable between first and second positions, said first position orienting said eyeshield to project downwardly from said arcuate hinge line such that said lower edge is adjacent the user's face so as to shield the eyes of the user, and to extend arcuately along said arcuate hinge line from said first side portion along the outer edge of said brim portion to said second side portion so as to wrap around the eyes of the user, said second position orienting said eyeshield to lie substantially flat against the brim portion with the lower edge of the eyeshield in proximity to the inner edge of the brim portion so as to store the shield when not shielding the user's eyes.

2. The apparatus of claim 1, wherein said visor is comprised of neoprene.

3. The apparatus of claim 1, wherein said eye shield is attached to the outer edge of said brim portion and said side portions, such that said eye shield covers the user's eyes and wraps around the sides of the user's head to form goggles.

4. The apparatus of claim 3, wherein said goggles are adapted to at least partially extend over the ears of the user.

5. The apparatus of claim 1, wherein said lens has a generally U-shape.

6. The apparatus of claim 1, wherein said lens is made from a curved strip of tinted Lexan TM.

7. The apparatus of claim 1, wherein said flexible body is substantially parabolic in shape and forms a visor.

8. The apparatus of claim 1, wherein said flexible body comprises a substantially crescent shaped sheet of material.

9. The apparatus of claim 1, further comprising a fastener attached to said flexible body, said fastener providing adjustability for mounting the apparatus on heads of different size.

10. The apparatus of claim 9, wherein said fastener is a hook and loop fastener, with a hook portion and a loop portion attached on opposite ends of the flexible body.

11. The apparatus of claim 1, wherein said flexible body has a substantially parabolic shape, said flexible body with said lens attached thereon forming sunglasses.

12. An article of headwear, as defined in claim 1, additionally comprising:
    a sheet of electrically responsive material mounted on said headwear in proximity to said side portions such that at least a portion of the electrically responsive material is free to acoustically vibrate; and
    at least one electrical lead connected to said electrically responsive material for conducting a signal which drives said material to vibrate in accordance with said signal to produce sound.

13. The apparatus of claim 12, wherein said sheet of electrically responsive material has at least one aperture therethrough.

14. An article of headwear, as defined in claim 1, additionally comprising:
    a piezoelectric speaker element comprising a sheet of piezoelectric material mounted at peripheral locations on a supporting structure such that a portion of said material interior to a periphery of said material is free to acoustically vibrate relative to said supporting structure, said supporting structure being attached to said headwear; and coupling means connected to said speaker element for conducting a signal which drives said material to vibrate in accordance with said signal to produce sound.

15. The apparatus of claim 14, additionally comprising a conductor which distributes said signal along a periphery of said film.

16. The apparatus of claim 14, further comprising:
a second piezoelectric speaker element attached to said flexible body, said second piezoelectric speaker element coupled to produce sound from a right channel signal; and
wherein said piezoelectric speaker element is coupled to produce sound from a left channel signal, said piezoelectric speaker element and second piezoelectric speaker element thereby producing stereo sound.

17. The apparatus of claim 14, wherein said piezoelectric speaker element has a layered construction including a sheet of piezoelectric film, a plurality of layers of conductive transfer tape and a backing sheet.

18. The apparatus of claim 14, further comprising:
a protective layer sized to cover a bottom side of said flexible body, said protective layer attached over the bottom side of said flexible body and said speaker element; and
wherein said piezoelectric speaker element is sized for placement between said flexible body and said protective layer.

19. The apparatus of claim 18, wherein said protective layer is fabric suitable for contact with the head.

20. The apparatus of claim 14, wherein said coupling means comprises conductor leads and an electrical connector.

21. The apparatus of claim 20, wherein said coupling means further comprises an amplifier to convert the signal output by the audio device for application to said piezoelectric speaker element, the input to said amplifier coupled to the output of said audio device and the output from said amplifier coupled to said connector.

22. The apparatus of claim 14, further comprising:
a lens adapted to improve the sound produced by said speaker element and partially block out sunlight, said lens attached to said flexible body; and
a nosepiece attached along an edge of said lens, said nosepiece shaped to conform to the bridge of the nose for a comfortable fit.

23. The apparatus of claim 22, wherein said nosepiece is a V-shaped strip of wetsuit material.

24. The apparatus of claim 14 further comprising a pair of ear pods, said ear pods attached and extending beneath said flexible body, said ear pods reflecting sound from said speaker element toward the ear of the user to enhance the sound produced by said speaker element.

25. The apparatus of claim 24, wherein each said ear pod comprises a reflecting member and a comfort strip, an upper edge of said reflecting member connected beneath the flexible body and a lower edge of said reflecting member connected to the comfort strip, said comfort strip and reflecting member forming an enclosure to direct the sound produced by said speaker element to the ears.

26. The apparatus of claim 25, wherein said reflecting members are a cupped sheet portion of Lexan TM and said comfort strips are wetsuit material.

27. The apparatus of claim 14, wherein said flexible body is a curved strip forming a headband, said flexible body having enlarged portions intermediate the distal ends of said flexible body, said enlarged portions adapted to cover the ears.

28. The apparatus of claim 27, wherein said flexible body is strip about 2 inches wide and said enlarged portions have a substantially circular shape about 4 inches in diameter.

29. An apparatus forming an item of wearing apparel, comprising:
a visor, formed from a sheet of a first material having first and second side portions and a brim portion therebetween, said brim portion having inner and outer edges;
an eye shield, formed from a sheet of a second material, said eye shield having an upper and lower edge; and
a flexible hinge for connecting said eye shield to said visor along an arcuate hinge line extending along and spaced from the outer edge of said brim portion a distance less than the distance from the inner edge of said brim portion, said hinge mounting said eye shield such that said eye shield has first and second positions, said first position orienting said eye shield to project from said brim so as to shield the eyes of a user such that said lower edge is generally adjacent the user's face, said second position orienting said eye shield against a surface of said visor to store said shield when not shielding the user's eyes.

30. The apparatus of claim 29, wherein said sheet of first material comprises neoprene.

31. The apparatus of claim 29, wherein said second material comprises transparent plastic.

32. The apparatus of claim 29, wherein said eye shield comprises tinting to reduce the light intensity reaching the user's eyes.

33. The apparatus of claim 29, wherein said visor is formed of a generally crescent shaped sheet of said first material and said eye shield is formed of a generally crescent shaped sheet of said second material.

34. The apparatus of claim 29, wherein said second material is lexan TM or mylar.

35. The apparatus of claim 29, wherein said first material is wetsuit material.

36. The apparatus of claim 29, wherein said eye shield is connected to said hinge along an arcuate edge of said eye shield, said arcuate edge being coextensive with said arcuate hinge line.

37. The apparatus of claim 29, wherein said hinge is formed by fabric attached to said visor and said eye shield.

38. An audio visor for producing sound from an audio device comprising:
a generally crescent shaped flexible body adapted for mounting on the head, said flexible body forming a visor;
said visor having a brim portion with an inner and outer edge;
a least one speaker element attached on a bottom side of said flexible body;
a protective layer sized to cover the bottom side of said flexible body, said protective layer attached over the bottom side of said flexible body and said speaker elements;
means for coupling said speaker elements to the audio device;
a fastener adapted to adjust the flexible body for mounting on heads of different size, said fastener connecting ends of said flexible body; and a generally U-shaped lens for protecting the eyes of the user having an upper and a lower edge, said lens arcuately wrapping around the sides of the head of the user, and the upper edge of said lens being attached to the outer edge of said brim at a hinge.

39. The apparatus of claim 38, wherein said speaker element comprises a sheet of piezoelectric film.

40. The apparatus of claim 39, wherein said film is rigidly mounted on said visor only along peripheral edges of said film to allow portions of said film to vibrationally move.

* * * * *